United States Patent [19]

Berney

[11] Patent Number: 5,777,303
[45] Date of Patent: Jul. 7, 1998

[54] DEVICE FOR ASSOCIATING TEST TUBE SAMPLES WITH ELECTRONIC LABELS FOR STORAGE OF IDENTIFYING DATA

[75] Inventor: Jean Claude Berney, Les Charbonnières, Switzerland

[73] Assignee: Gay Freres, Vente et Exportation S.A., Geneva, Switzerland

[21] Appl. No.: 633,747

[22] PCT Filed: Sep. 5, 1995

[86] PCT No.: PCT/CH95/00190

§ 371 Date: Apr. 24, 1996

§ 102(e) Date: Apr. 24, 1996

[87] PCT Pub. No.: WO96/07479

PCT Pub. Date: Mar. 14, 1996

[30] Foreign Application Priority Data

Sep. 9, 1994 [CH] Switzerland .................. 2767/94-6

[51] Int. Cl.⁶ .................................................. G06F 17/00
[52] U.S. Cl. .................. 235/375; 235/385; 235/441; 235/486; 235/487; 422/104
[58] Field of Search .................. 235/375, 385, 235/439, 441, 451, 486, 492, 487; 422/102, 104

[56] References Cited

U.S. PATENT DOCUMENTS

| 3,619,568 | 11/1971 | Taplin ..................... 235/375 X |
| 3,680,967 | 8/1972 | Engelhardt ..................... 356/246 |
| 3,818,188 | 6/1974 | Hertel et al. ..................... 235/61.11 R |
| 3,831,006 | 8/1974 | Chaffin, III et al. ..................... 235/375 |
| 4,164,320 | 8/1979 | Irazoqui et al. ..................... 235/375 |
| 4,614,366 | 9/1986 | North et al. ..................... 235/375 X |
| 4,628,193 | 12/1986 | Blum ..................... 235/375 |
| 4,678,894 | 7/1987 | Shafer ..................... 235/375 |
| 4,839,875 | 6/1989 | Kuriyama et al. ..................... 235/375 X |
| 4,857,716 | 8/1989 | Gombrich et al. ..................... 235/375 X |
| 5,059,951 | 10/1991 | Kaltner ..................... 235/375 X |
| 5,156,032 | 10/1992 | Edgar ..................... 235/375 X |
| 5,357,095 | 10/1994 | Weyrmich et al. ..................... 235/375 X |
| 5,378,433 | 1/1995 | Duckett et al. ..................... 422/104 X |
| 5,381,487 | 1/1995 | Shamos ..................... 235/375 X |
| 5,397,542 | 3/1995 | Nelms et al. ..................... 422/104 |
| 5,401,110 | 3/1995 | Neeley ..................... 235/375 X |
| 5,437,841 | 8/1995 | Balmer ..................... 422/104 X |
| 5,508,499 | 4/1996 | Ferrario ..................... 235/375 |
| 5,539,188 | 7/1996 | Fallah et al. ..................... 235/375 |
| 5,579,928 | 12/1996 | Anukwuem ..................... 422/104 X |
| 5,583,330 | 12/1996 | Fallah et al. ..................... 235/375 X |
| 5,587,578 | 12/1996 | Serra ..................... 235/375 X |
| 5,607,187 | 3/1997 | Salive et al. ..................... 235/375 X |

FOREIGN PATENT DOCUMENTS

| 2 555 744 | 5/1985 | France . |
| 27 58 437 | 7/1979 | Germany . |
| 43 06 563 | 9/1994 | Germany . |
| 89-08264 | 9/1989 | WIPO . |
| 95-28713 | 10/1995 | WIPO . |

OTHER PUBLICATIONS

WPI Abstract of DE-OS 43 06 563, Lichtenberg, Meyer, & Grunwald.

Primary Examiner—Donald T. Hajec
Assistant Examiner—Michael G. Lee
Attorney, Agent, or Firm—Milton Oliver

[57] ABSTRACT

The present invention relates to a system which permits securing an electronic label on a test tube with the aid of a detachable support. The support allows also an easy connection between the label and a device for reading/writing the label, allowing a registration of the entirety of useful information of, for example, a blood analysis and a transfer of content of the label to a computer-assisted data base for data-treatment and storage.

10 Claims, 3 Drawing Sheets

5,777,303

1

DEVICE FOR ASSOCIATING TEST TUBE SAMPLES WITH ELECTRONIC LABELS FOR STORAGE OF IDENTIFYING DATA

FIELD OF THE INVENTION

It is well known that in the medical field and in the chemical industry, a very important number of analyses is performed and beyond them, a substantial amount of analyses is made in test tubes, preferentially in test tubes made from glass. In most cases, said analyses are supervised very carefully, in order to prevent errors which can have important consequences. Blood analyses, for example, concern problems relating to AIDS.

BACKGROUND

It is therefore necessary, to be enabled to register all the useful information during an analyses for the proper execution of the latter. Said information is stored, allowing to establish a traceability of the entirety of the operations performed. Nowadays, said information is most often jotted down in a manuscript-like manner and, subsequently, transferred manually to a computer-assisted data base, resulting in important error risks with regards to the jotting down and to the transfer.

SUMMARY OF THE INVENTION

The device for the information registration and for the information transfer for test tube analyses according to the present invention, allows to minimize such risks by eliminating of the jotting down and of the manual transfer. Said device comprises at least one electronic memory label and means for reading or reading/writing said labels. Said labels are mounted on supports being provided to fix said labels onto said test tubes during the time of analysis and to reassure the positioning and the connection of said labels to said means for reading/writing during the registration and the transfer of information.

BRIEF FIGURE DESCRIPTION

DETAILED DESCRIPTION

Figure 1:
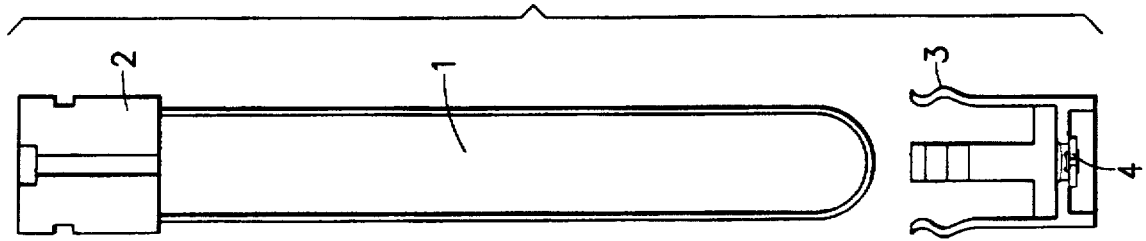
FIG. 1 shows exemplary embodiment of a label and a support, allowing to fix said label on test tube.

FIG. 1 shows an exemplary embodiment of a test tube 1 having a cap 2 of that kind used for blood analyses. A metallic support 3, on which is mounted an electronic label 4, can be fixed on a test tube extremity during the time of analysis. Said electronic label 4 allows a registration of all useful information required for said analysis, in particular, information relating to the person under concern, to basis reference data, to the analysis data and to the result data, to the used analysis apparatus, to the service staff, etc.

Figure 2:
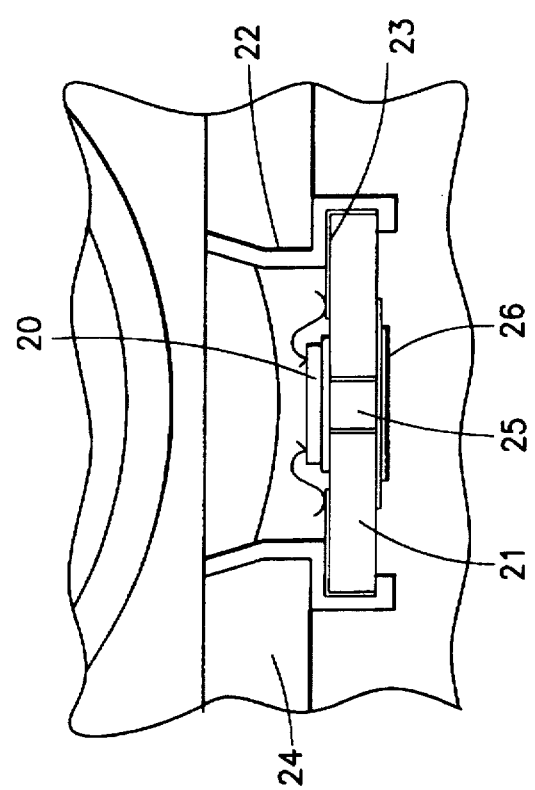
FIG. 2 shows an exemplary configuration of an electronic label having contacts and which can be used within the scope of the invention.

The configuration of the label is shown in an exemplary embodiment according to FIG. 2. In particular, the label has two contacts like that described in the international application WO 95/28713, publ. Oct. 26, 1995, and corresponding U.S. Ser. No. 08/557,027. Said label comprises an integrated circuit 20 being connected by bonding to an insulating interconnection circuit 21. The latter is, for example, a printed circuit board (PCB). The label is mounted on a metallic case 22 which is interconnected with the aid of a metallic zone 23 of the interconnection circuit 21 to one of the power supply contacts of the integrated circuit 20. Said metallic case 22 is mounted in a hole of the metallic support 24, in such a way, that the latter is also interconnected electrically to said first power supply contact of the integrated circuit 20. The second contact of the integrated circuit 20 is interconnected with the aid of a metallic hole 25 to a contact zone 26 of the interconnection circuit 21. It is therefore possible, to establish an interconnection between the integrated memory circuit 20 via the central contact 26 and the metallic body of the support 24.

Figure 3:
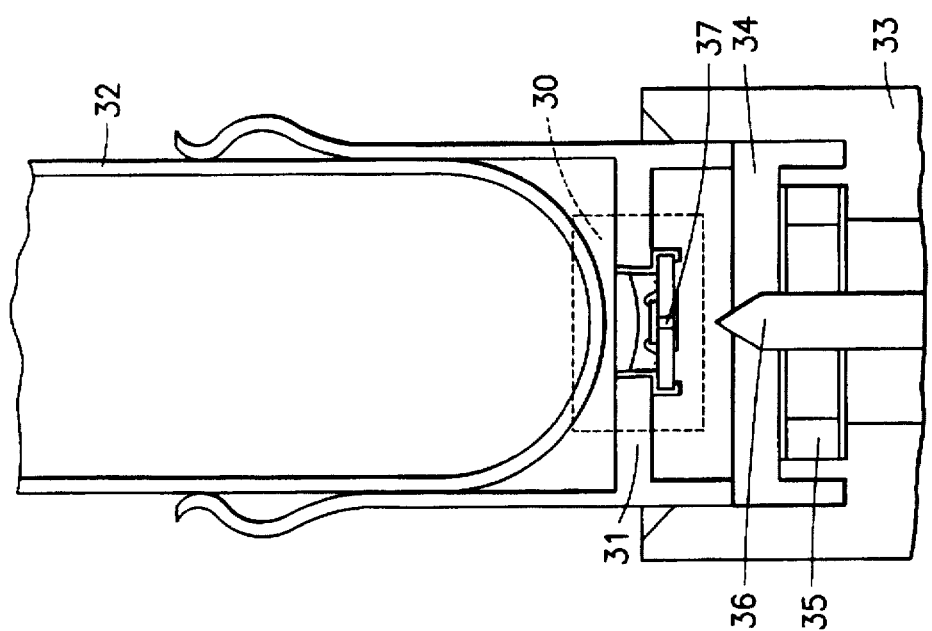
FIG. 3 shows in an exemplary manner the positioning and the connection of a label according to FIG. 2 to means for reading/writing said label with the helps of a support.

FIG. 3 shows in an exemplary manner the positioning and the connection of a label according to FIG. 2 to means for reading/writing said label with the helps of the support 31. The electronic label according to FIG. 2 is shown within a frame 30. Said label 30 is mounted on the metallic support 31. The extremities of the support 31 have a spring-like shape, allowing a firm fixation of said label 30 onto the test tube 32 during the time of analysis. Moreover, the metallic support 31 reassures the positioning and the connection to means for reading/writing the label 30 as will be described in the following.

In order to read or modify the content of the electronic label 30, the test tube 32 and its support 31 are placed on a set-up for reading/writing. Said set-up consists of a metallic base 33 into which is drilled a guiding hole 34 having a diameter slightly larger than the diameter of the support 31. A magnet 35 is arranged on the bottom of the guiding hole 34. After setting the metallic support 31 on the set-up and next to the magnet 35, the support 31 and the magnet 35 are attracted by an attractive power, allowing to maintain the position of said support 31 and of the test tube 32. A connection of the means for reading/writing to the electronic label 30 is made with the aid of a spring contact 36 of the set-up. Said spring contact 36 faces the central contact 37 of the electronic label 30. A ground connection of the means for reading/writing to the electronic label 30 is made via a direct contact between the metallic support 31 and the metallic base 33 of the set-up. Said fixation of the support 31 onto a set-up with the aid of a magnet 35 is only one exemplary possibility. It is of course possible to use an entirely mechanical configuration, such as a bayonet catch. The means for reading/writing can comprise set-ups for a plurality of test tubes 32 as will be described on the following figure.

The set-up according to FIG. 3 is made for a label 30 having two co-axial contacts. It is obvious to one of ordinary skill in the art to use also memory labels having a plurality of contacts, such as those used in chip cards. It is therefore possible, to use a configuration with a plurality of contacts, having for example a plurality of concentric contacts. It is also possible to use a combination of a plug with a power point, the plug being mounted on the set-up 33 and the power-point being mounted on the support 31, or vice versa.

Figure 4:
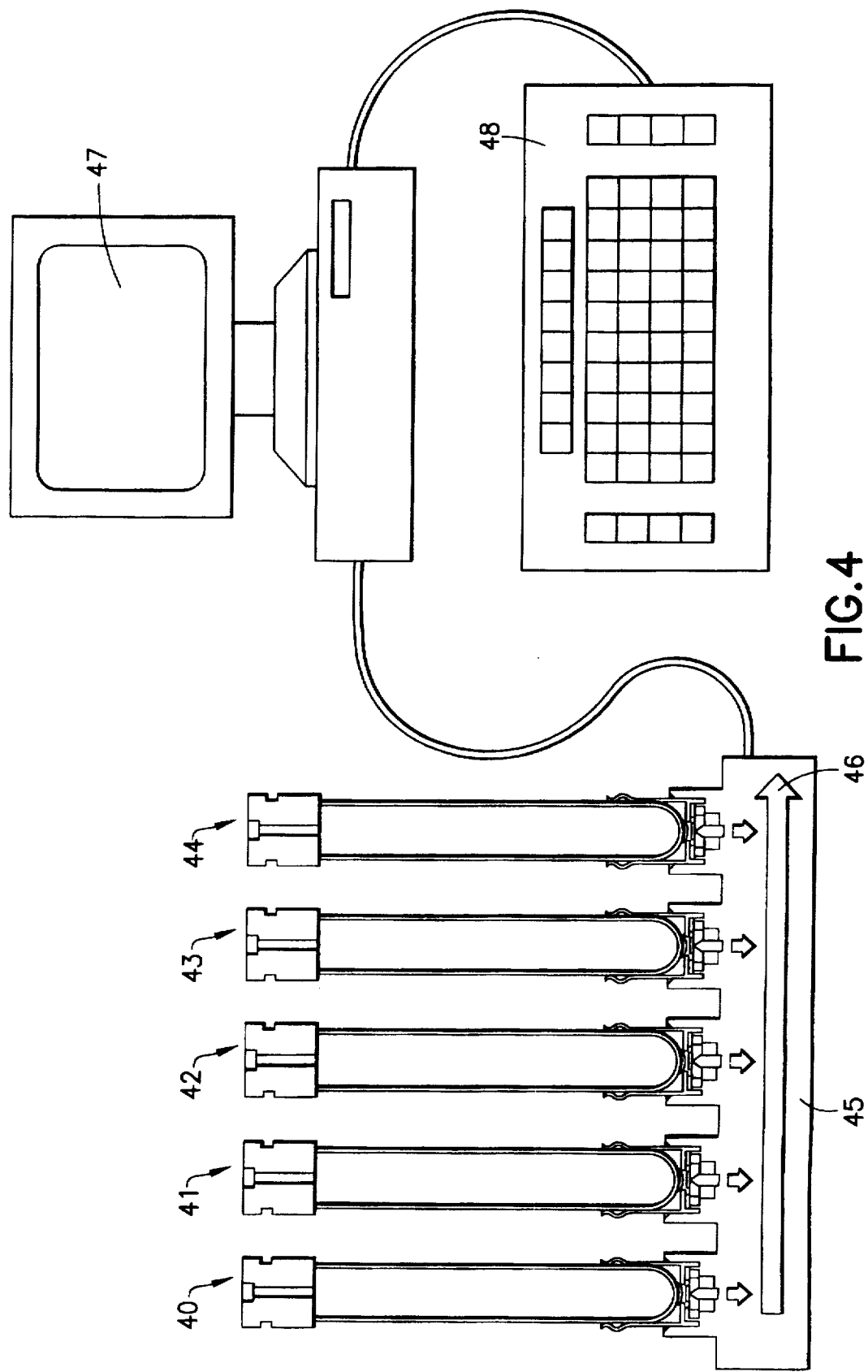
FIG. 4 shows an exemplary embodiment of means for reading/writing for a plurality of test tubes being equipped with electronic labels mounted on supports and FIG. 4 shows an exemplary embodiment of means for the registration and for the transfer of information.

FIG. 4 shows an exemplary embodiment of means for reading/writing of a plurality of test tubes 40, 41, 42, 43 and 44 being equipped with electronic labels mounted on their supports. Said means for reading/writing comprise a base 45, on which are mounted as many individual set-ups as there are labels to be read or to be written to. Each of said individual set-ups is interconnected to a bus-system 46 being represented in a very schematic manner. Such a bus-system can be a manual commutation system, allowing to establish a contact to a desired label or it can be a more sophisticated system, being controlled from a distance, being for example controlled via the computer system. For this purpose, the bus-system 46 is interconnected to the computerized information processing system. The latter is schematically represented by a computer 47 and by its keyboard 48. It is therefore possible, to control the entirety of the operations relating to the reading and to the transfer of information within the labels under concern with the aid of the keyboard 48 and via computer program menus, allowing to reduce error risks to a minimum. In order to perform, for example, a blood analysis, firstly the reference data of the patient under concern and the kind and number of analyses to be performed are fed directly from a central data base into the label. Secondly the date of analysis, the used analysis apparatus, the name of the service operator, the result data, etc are registered. Finally all this information is transferred to the centralized data bank of the patient.

Figure 5:
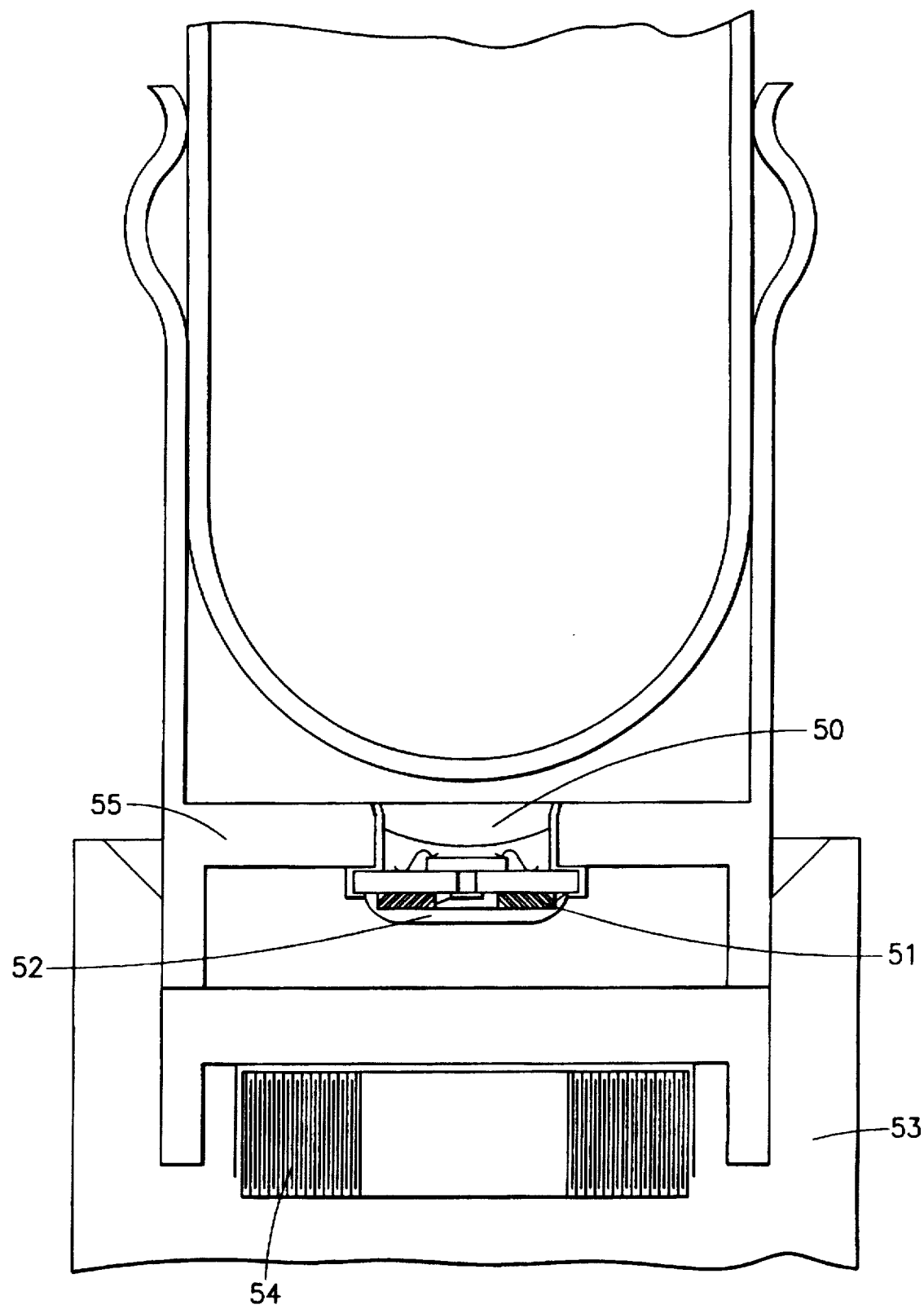
FIG. 5 shows an exemplary configuration of an electronic label being accessible via radiofrequencies (RF) and which can be used within the scope of the invention.

FIG. 5 shows an exemplary configuration of an electronic label 50 being accessible via radiofrequencies (RF) and which can be used within the scope of the invention. As distinct from the preceding figures, which described devices using labels with contacts, it is of course also possible to use other kinds of electronic labels, especially labels being read from distance. This is the case for radiofrequency labels, which use a magnetic coupling. In order to obtain such a coupling, the label 50 comprises a coil 51 which is mounted on the external side of the interconnection circuit and protected by a droplet of resin 52. The set-up 53 itself comprises another coil 54. After setting the metallic support 55 on the set-up 53, the two coils 51 and 54 which are next to each other, allow reading or reading/writing operations. Said operations are known to one of ordinary skill in the art and won't be described.

There exist of course other possible embodiments of the device according to the invention. However, their description would contribute nothing toward the comprehension of the latter.

What is claimed is:

1. Device for registering and for transferring information relating to test tube analyses, comprising at least one electronic memory label mounted on a metallic case, a metallic support formed with a metallic hole therein, said label being electrically accessible via said metallic hole, and means for reading or reading/writing said label, wherein said labels are mounted on supports which secure each label onto a respective test tube during time of analysis and to assure positioning and connection of said labels to said means for reading/writing during the registration and the transfer of said information.

2. Device according to claim 1, wherein said supports are cylindrical and secure within respective guiding holes of corresponding set-ups coupled to said means for reading/writing.

3. Device according to claim 2, wherein said set-ups of means for reading/writing further comprise a locking system for said supports.

4. Device according to claim 1, wherein said supports comprise a spring portion which engages said test tube, thereby securing said supports onto a cylindrical portion of said test tube.

5. Device according to claim 1, said supports place connection means, of said means for reading/writing, between said labels and said means for reading/writing, within axis of said test tubes.

6. Device according to claims 1, wherein connection means of said means for reading/writing, being placed between said labels and said means for reading/writing, are positioned within axis of the test tube with aid of said supports, and form electrical contacts.

7. Device according to claim 6, wherein one of the electrical contacts is supported by a body of said supports.

8. Device according the claims 1, wherein connection means of said means for reading/writing, being placed between said labels and said means for reading/writing, are positioned within axis of the test tube with aid of said supports and form a magnetic coupling.

9. Device according to claim 1, wherein said means for reading/writing comprise a base on which is mounted a plurality of set-ups, each of said set-ups corresponding to a support having a test tube and commutation means allow to establish a contact to a desired label.

10. Device according to claim 1, wherein said means for reading/writing are connected to a database provided to control commutation means, allowing to establish a contact to a desired label.

* * * * *